United States Patent [19]

Clark

[11] Patent Number: 4,791,125
[45] Date of Patent: Dec. 13, 1988

[54] THIAZOLIDINEDIONES AS HYPOGLYCEMIC AND ANTI-ATHEROSCLEROSIS AGENTS

[75] Inventor: David A. Clark, East Lyme, Conn.

[73] Assignee: Pfizer Inc., New York, N.Y.

[21] Appl. No.: 127,831

[22] Filed: Dec. 2, 1987

[51] Int. Cl.$^4$ ............... C07D 491/052; A61K 31/425
[52] U.S. Cl. ...................................... 514/369; 548/183
[58] Field of Search ..................... 548/183; 514/369

[56] References Cited

U.S. PATENT DOCUMENTS

| | | | |
|---|---|---|---|
| 4,287,200 | 9/1981 | Kawamatsu et al. | 424/270 |
| 4,340,605 | 7/1982 | Kawamatsu et al. | 424/263 |
| 4,438,141 | 3/1984 | Kawamatsu et al. | 424/248 |
| 4,444,779 | 4/1984 | Kawamatsu et al. | 424/263 |
| 4,461,902 | 7/1984 | Kawamatsu et al. | 548/183 |
| 4,572,912 | 2/1986 | Yoshioka et al. | 514/369 |
| 4,617,312 | 10/1986 | Schnur | 514/369 |
| 4,687,777 | 8/1987 | Meguro et al. | 514/342 |
| 4,703,052 | 10/1987 | Eggler et al. | 514/337 |

FOREIGN PATENT DOCUMENTS 1036284 2/1986 Japan ..................................... 548/183

Primary Examiner—Robert Gerstl
Attorney, Agent, or Firm—Peter C. Richardson; J. Trevor Lumb; Gregg C. Benson

[57] ABSTRACT

The present invention relates to certain compounds of the formula

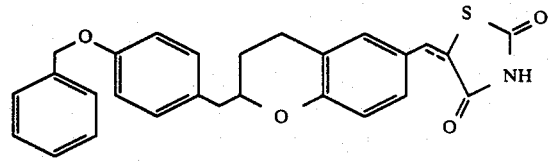

wherein the broken line is a bond or no bond, and the pharmaceutically acceptable cationic salts thereof having utility as hypoglycemic and anti-atherosclerosis agents, methods for their use and pharmaceutical compositions containing them.

10 Claims, No Drawings

THIAZOLIDINEDIONES AS HYPOGLYCEMIC AND ANTI-ATHEROSCLEROSIS AGENTS

BACKGROUND OF THE INVENTION
1. Field of the Invention

The present invention relates to certain compounds of the formula

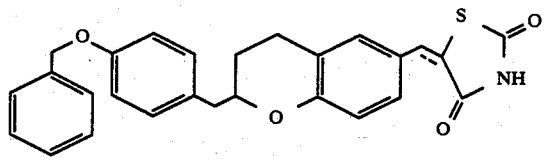

wherein the broken line is a bond or no bond, and the pharmaceutically acceptable cationic salts thereof having utility as hypoglycemic and anti-atherosclerosis agents, methods for their use and pharmaceutical compositions containing them.

2. General Background

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily, usually self, injection. Determination of the proper dosage of insulin requires frequent estimations of the sugar in the urine or in the blood. The administration of an excess dose of insulin causes hypoglycemia, with effects ranging from mild abnormalities in blood glucose to coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed recently by Blank [Burger's Medicinal Chemistry, Fourth Edition, Part II, John Wiley and Sons, N.Y. (1979), pp. 1057-1080].

U.S. Pat. No. 4,342,771 discloses a class of oxazolidinedione hypoglycemic agents of the general formula

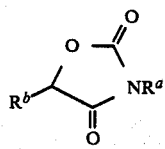

where $R^a$ is H or certain acyl groups and $R^b$ is certain mono- or bicyclic heterocyclic groups.

U.S. Pat. No. 4,617,312 discloses a group of 5-phenyl-thiazolidine-2,4-dione hypoglycemic agents of the formula

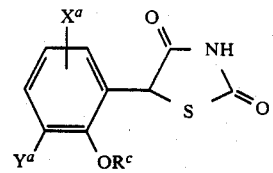

where $R^c$ is lower alkyl, $X^a$ is F, Cl or Br and $Y^a$ is H, Cl, lower alkyl or lower alkoxy.

U.S. Pat. No. 4,461,902 discloses certain 5-[(4-cyclohexylmethoxyphenyl)methyl]thiazolidine-2,4-dione hypoglycemic agents of the formula

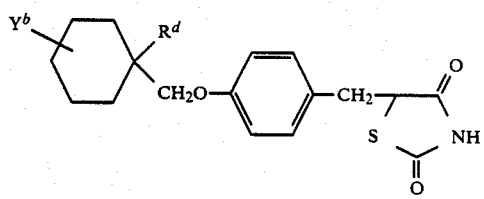

where $R^d$ is H or lower alkyl and $Y^b$ is an oxo or hydroxy group.

U.S. Pat. No. 4,703,052 discloses certain hypoglycemic thiazolidinediones of the formula

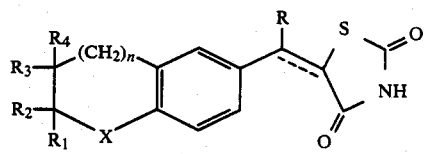

or a pharmaceutically acceptable cationic salt thereof, wherein the broken line is a bond or no bond, n is zero, 1, or 2; X is O, S,

$CH_2$, $C=O$, $CHOH$ or $NR_5$ where $R_5$ is H, formyl, $(C_2-C_5)$alkanoyl, benzyloxycarbonyl, $CO(CH_2)_xC_6H_5$ where x is an integer from 1 to 3, $(C_1-C_6)$alkyl, said alkyl optionally substituted by HO, Cl, Br, $OCH_3$, phenyl or $COOR_6$ where $R_6$ is $(C_1-C_4)$alkyl;

R is H, $CH_3$ or $C_2H_5$;

when taken separately, $R_1$ is H, $(C_5-C_7)$cycloalkyl, $(C_6-C_8)$methylsubstituted cycloalkyl, pyridyl, thienyl, furyl, naphthyl, p-biphenylyl, tetrahydrofuranyl, tetrahydropyranyl, tetrahydrothienyl, $C_6H_4W_2$ or alk-$W_1$ and alk is $(C_1-C_6)$alkylene, ethylidene or isopropylidene; $W_1$, is H, OH, $(C_1-C_4)$alkoxy, $(C_1-C_4)$thioalkyl, pyridyl, furyl, thienyl, tetrahydrofuryl, tetrahydrothienyl, naphthyl, $(C_5-C_7)$cycloalkyl or $C_6H_2W_2$ and $W_2$ is H, OH, F, Cl, Br, $(C_1-C_4)$alkyl, $(C_1-C_4)$alkoxy or $(C_1-C_4)$thioalkyl; $R_2$ is H or $CH_3$, $R_3$ is H, $(C_1-C_6)$alkyl, $C_6H_4W_2$ or benzyl; and $R_4$ is H;

when $R_1$ and $R_2$ are taken together they form $(C_4-C_6)$ alkylene and $R_3$ and $R_4$ are each H;

when $R_3$ and $R_4$ are taken together they form $(C_4–C_6)$ alkylene and $R_1$ and $R_2$ are each H; and when $R_2$ and $R_3$ are taken together they are $(C_3–C_4)$alkylene and $R_1$ and $R_4$ are each H.

Certain 5RS racemic and 5R optically active oxazolidine-2-one compounds of the formula

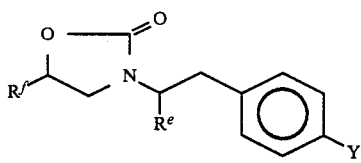

wherein
$R^f$ is

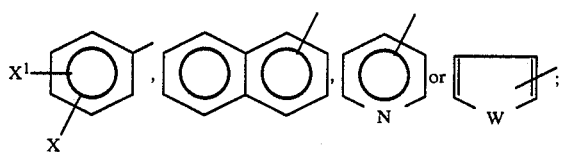

W is sulfur or oxygen;
X and $X^1$ are each independently H, Cl, F or $CF_3$;
Y is inter alia

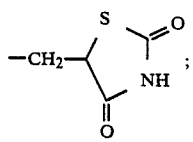

$R^e$ is H or $CH_3$;

and certain pharmaceutically acceptable salts thereof are disclosed in international patent application No. PCT/US87/01356 which is assigned to and has been filed in the name of the assignee hereof. That patent application also discloses the use of such compounds as hypoglycemic agents and, further, the use of some, if not all, of such compounds to lower blood cholesterol levels.

Atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

SUMMARY OF THE INVENTION

The invention concerns the novel thiazolidinediones of the formula

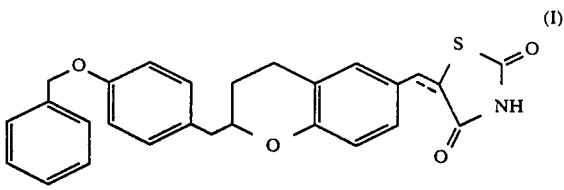

wherein the broken line is a bond or no bond, and the pharmaceutically acceptable cationic salts thereof.

The compounds of the invention are useful as hypoglycemic agents and are mechanistically distinct from known hypoglycemics (the sulfonylureas) currently employed in diabetic therapy. The compound of formula (I) wherein the broken line is no bond is preferred as such a hypoglycemic agent. Further, the compound of formula (I) wherein the broken line is no bond is, in addition to its hypoglycemic activity, useful as an anti-atherosclerosis agent through its ability to lower serum cholesterol levels in mammals.

Mixtures of optically active isomers and partially or completely optically resolved isomers of the compounds claimed herein are within the scope of the present invention.

Also embraced by the present invention are pharmaceutical compositions for use in (a) treating a hyperglycemic mammal which comprises a blood glucose lowering amount of a compound of formula (I) and a pharmaceutically acceptable carrier and/or (b) lowering blood serum cholesterol levels which comprises a blood serum cholesterol lowering amount of a compound of formula (I) where the broken line is no bond and a pharmaceutically acceptable carrier. The invention further comprises a method of lowering blood glucose in a hyperglycemic mammal which comprises administering to a mammal in need of such treatment a blood glucose lowering effective amount of a compound of formula (I). Further still, the invention comprises a method of lowering blood glucose and/or blood serum cholesterol levels in a mammal which comprises administering to a mammal in need of such treatment a blood glucose and/or serum cholesterol lowering effective amount of The compounds of formula (I) contain an asymmetric center at the 2-position. The compound of formula (I) (wherein the broken line is no bond) has an additional asymmetric center at the 5-carbon of the thiazolidinedione group. Among the enantiomers of a given compound, one will ordinarily be favored over the others and the racemates because of its greater activity. The present invention is considered to be embracive of the racemates, diastereomeric mixtures, the pure enantiomers and diastereomers of the compounds of formula (I), the utility of which is determined by the biological evaluations described below.

DETAILED DESCRIPTION OF THE INVENTION

The compounds of the invention are prepared, for example, by the method shown in Synthetic Scheme A, below.

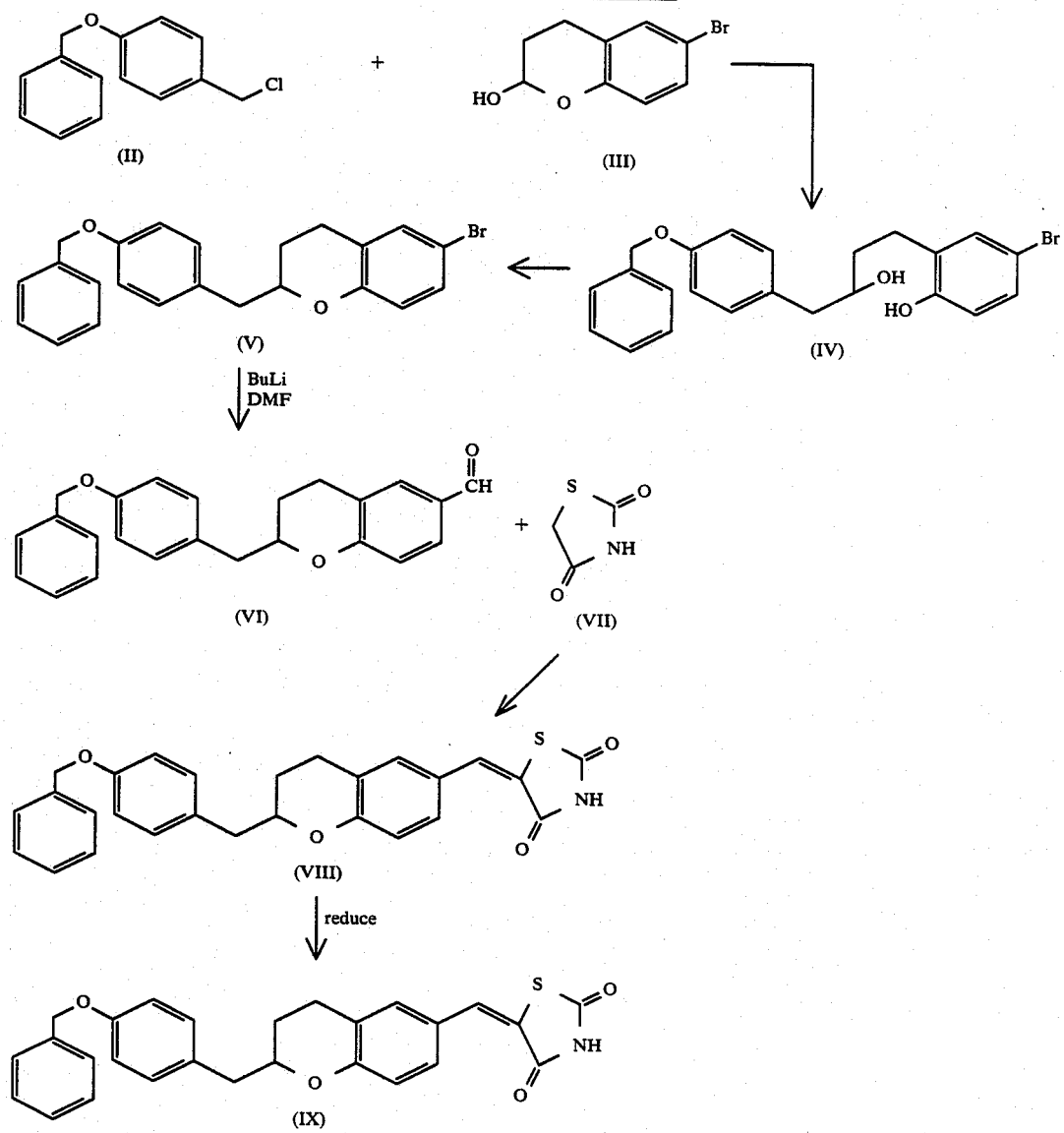

a compound of formula (I) where the broken line is no bond.

In the first step of the above synthetic scheme, an approximately four-fold excess of reactant II is converted into the corresponding Grignard reagent by gentle reflux of a solution of reactant II in an inert solvent to which has been added magnesium suspended in ether. The resulting Grignard reagent is reacted with reactant III over a temperature range of $-25°$ C. to 50° C. with a preferable temperature in the range of $-10°$ C. to room temperature.

The benzyloxyphenylmethyl alcohol-phenol (IV) which is produced as a result of the first step is then converted to the corresponding benzopyran compound of formula (V) by refluxing the compound of formula (IV) in toluene in the presence of p-toluenesulfonic acid.

The benzopyran of formula (V) in a reaction inert solvent is then reacted with approximately equimolar amounts of n-butyllithium and dimethylformamide at about $-78°$ C. to produce the aldehyde of formula (VI).

In the next step, approximately equimolar amounts of the aldehyde of formula (VI) and the thiazolidinedione of formula (VII) are heated in the presence of a mild base to provide the olefin of formula (VIII). While this step may be carried out in the presence of a reaction inert solvent, it is preferably carried out in the absence of solvent at a temperature which is sufficiently high to cause at least partial melting of the reaction mixture. A preferred such temperature is in the range of from 100° to 250° C., and especially preferred is a temperature of from 140° to 200° C.

Examples of suitable mild bases for the above reaction include the alkali metal and alkaline earth salts of weak acids such as the ($C_1$–$C_{12}$) alkyl carboxylic acids and benzoic acid; alkali metal and alkaline earth carbonates and bicarbonates such as calcium carbonate, magnesium carbonate, potassium bicarbonate; and tertiary amines such as pyridine, N-methylmorpholine, N-ethylpiperidine and the like. An especially preferred mild base is sodium acetate for reasons of economy and efficiency.

In a typical such reaction the aldehyde starting material (VI) and thiazolidinedione (VII) are combined in approximately equimolar amounts with a molar excess, preferably a 2-4 fold molar excess, of anhydrous sodium acetate and the mixture is heated at a temperature high enough to effect melting, at which temperature the reaction is substantially complete in from about 5 to 60 minutes. The desired olefin of formula (VIII) is then isolated, for example, by mixing with water and filtration, to obtain the crude product, which is purified, if desired, e.g. by crystallization or by standard chromatographic methods.

The olefinic product of formula (VIII) is an active hypoglycemic agent and also serves as intermediate for preparation of the corresponding reduced compound of formula (IX). The reduction of the above olefin may be carried out by employing a wide variety of reducing agents which are known to reduce carbon-to-carbon double bonds. However, since hydrogenation methods have a well-known tendency to cleave benzylic carbon-oxygen bonds, a preferred method for reduction of the compounds of formula (VIII) is conventional sodium amalgam reduction in methanol, usually at or about ambient temperature, as exemplified below.

When the reduction is substantially complete, the desired product of formula (IX) is then isolated by filtration, the solvent evaporated and the product purified, if desired, by well known methods such as crystallization or by chromatography.

The expression "pharmaceutically acceptable cationic salts" as used herein is intended to define such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, etc. An especially preferred such salt is the sodium salt.

The pharmaceutically acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and addition of a non-solvent.

4-Benzyloxybenzyl chloride (II) and 2,4-thiazolidinedione (VII) are commercially available. 6-Bromo-2-chromanol (III) is prepared according to the procedure described in U.S. Pat. No. 4,703,052 (Preparation K), the teachings of which are incorporated herein by reference.

The reactions employed to prepare the compounds of this invention can generally be monitored by standard tlc methods, employing commercially available plates. Suitable eluants are common solvents such as chloroform, ethyl acetate or hexane or suitable combinations thereof which will differentiate starting materials, products, by-products, and in some cases intermediates. Applying these methods, which are well known in the art, will permit further improvement in the methodology of the specific examples detailed hereinafter, e.g. the selection of more optimal reaction times and temperatures, as well as aid in the selection of optimal processes.

The thiazolidine-2,4-diones of the present invention are readily adapted to clinical use as antidiabetic agents and/or anti-atherosclerosis agents.

The activity required for the clinical use as antidiabetic agents is defined by the test for hypoglycemic effect in ob/ob mice by the following procedure:

Six to eight week old C57 BL/6J-ob/ob mice (obtained from Jackson Laboratories, Bar Harbor, Me.) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for glucose analysis. Animals were then dosed daily for four days with drug (10 mg/kg) or vehicle. All drugs were administered in a vehicle consisting of 0.25% (w/v) methylcellulose in water with no pH adjustment. Animals were bled 24 hours after the fourth administration of drug or vehicle (via the ocular route) for blood glucose levels. The weight of each animal was recorded on days 1 and 5 of the treatment. The freshly collected samples (125 microliters in 330 microliter tubes) were centrifuged for two minutes at 10,000 xg at room temperature. A 50 microliter sample was analyzed for glucose, for example, by the ABA 200 Bichromatic Analyzer*, using the A-gent* glucose UV reagent system# (hexokinase method) using 100, 300 and 500 mg/dl standards. Plasma glucose was then calculated by the equation,

*Plasma glucose (mg/dl) = Sample value × 5 × 1.78 = 8.9 × Sample value* where 5 is the dilution factor and 1.78 is the plasma hematocrit adjustment (assuming the hematocrit is 44%).

*A registered trademark of Abbott Laboratories, Diagnostics Division, 820 Mission Street, So. Pasadena, CA 91030.
A modification of the method of Richterich and Dauwalder, Schweizerische Medizinische Wochenschrift, 101, 860 (1971).

The conclusion that the compound of formula (I) wherein the broken line is no bond also possesses valuable cholesterol lowering properties is based on the following study.

Mice (strain C57BR/cd J), obtained from Jackson Laboratories, Bar Harbor, Me., were used at age 6–12 weeks, following 2–4 weeks acclimation in our laboratories, having free access to water and standard laboratory chows. Animals were divided randomly into three groups of 6–8 animals. One group was maintained on the standard laboratory chow. The remaining two groups were placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin mix for 18 days; and dosed daily at 9–11 a.m. for the final 5 days by oral gavage, the control group with 5 ml/kg of vehicle (0.25% methyl cellulose) and the test group with drug (20 mg/kg in vehicle). After the fourth day of dosing, the animals were fasted overnight, starting at 5 p.m. The following morning a fifth and final dose of the drug was administered to the test group and three hours later the animals sacrificed by decapitation. Blood from the body trunk was collected and allowed to clot, and the serum assayed enzymatically, using an Abbott VP automated analyzer, for HDL cholesterol, LDL and VLDL cholesterol, and total cholesterol.

The thiazolidine-2,4-diones of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administraiton is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or a pharmaceutically acceptable cationic salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously, or intramuscularly, with intramuscular administration being preferred in man.

The following Examples serve to illustrate the invention and are not to be construed as limiting the invention to those embodiments so exemplified. Proton magnetic resonance spectra were measured at 60 MHz for solutions in deuterochloroform ($CDCl_3$) and peak positions are expressed in parts per million (ppm) downfield from tetramethylsilane. The following abbreviations are used: s, singlet; m, multiplet.

EXAMPLE 1

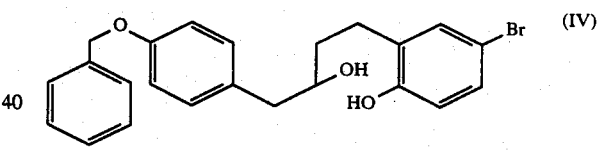

Magnesium mesh (0.25 mole, 6.0 g) was suspended in 25 ml of ether at room temperature. 4-Benzyloxybenzyl chloride (0.098 mole, 22.7 g) was dissolved in 100 ml of tetrahydrofuran and added to the magnesium suspension over a period of 15 minutes at gentle reflux temperature. The mixture was stirred for an additional 15 minutes at gentle reflux temperature and then cooled to −10° C. 6-Bromo-2-chromanol (0.024 mole, 5.4 g) was dissolved in 25 ml of tetrahydrofuran and added to the reaction mixture over a 15 minute period. The reaction was warmed to room temperature and stirred for one (1) hour. Then, the reaction was diluted with 50 ml of 10% HCl and extracted with ethyl acetate (2×150 ml). The combined organic phases were washed with 50 ml of 10% $NaHCO_3$, then 50 ml of saturated NaCl, dried over $MgSO_4$ and stripped of solvent in vacuo. The residue was purified on silica gel using hexane/ethyl acetate (3:1) as eluent to afford 8.3 g of the compound of formula (IV) as a gum which was used in the synthesis shown in Example 2, below.

$^1$H-NMR($CDCl_3$)ppm(delta): 1.8 m (2H), 2.6–2.8m (4H), 3.7 m (1H), 3.8–3.9 m (2H, OH), 5.0 s (2H), 6.7–7.5 m (12H).

EXAMPLE 2

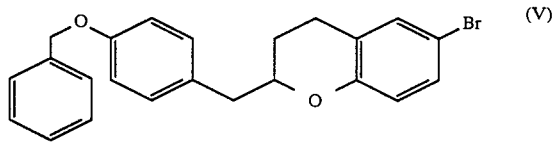

The compound of formula (IV) obtained in Example 1 (8.3 g) was heated to reflux temperature in 500 ml of toluene in the presence of 1.1 g of p-toluenesulfonic acid monohydrate with a Dean Stark trap for three (3) hours. The reaction mixture was cooled and washed with 100 ml of 10% NaHCO$_3$ followed by 100 ml of saturated NaCl, then dried over MgSO$_4$. The solvent was then removed in vacuo. The residue was crystallized from hexane/ether to afford 5.1 g of the benzopyran of formula (V) above as a solid, m.p. 135°–136° C.

EXAMPLE 3

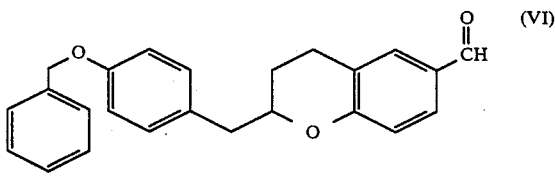

4.5 g (11 mmole) of the benzopyran of formula (V), prepared as shown in Example 2, was dissolved in 200 ml of tetrahydrofuran and cooled to 78° C. Then, N-butyllithium (11 mmole, 5.25 ml of a 2.1M solution in hexane) was added and the solution was stirred for one (1) hour. Dimethylformamide (11.0 mmole, 804 mg) was then added and the reaction mixture was stirred for an additional hour at −78° C. Then, 50 ml of 10% HCl was added and the solution was warmed to room temperature and extracted with ethyl acetate (2×100 ml). The combined organic phases were washed with 50 ml of saturated NaCl, dried over MgSO$_4$ and the solvents were removed in vacuo. The residue was triturated with hexane to afford 1.6 g of the aldehyde of formula (VI) as a solid, m.p. 162°–163° C.

EXAMPLE 4 dl-5-[(2-(4-benzyloxyphenylmethyl)-3,4-dihydro-2H-benzopyran-6-yl)methylene]thiazolidine-2,4-dione The aldehyde of formula (VI) prepared as shown in Example 3 (4.4 mmole, 1.6 g), 2,4-thiazolidinedion (5.0 mmole, 585 mg) and sodium acetate (11.0 mmole, 902 mg) were heated neat at 170° C. for 45 minutes. The mixture was cooled and triturated with water followed by methylene chloride to afford 1.3 g of the title compound as a solid, m.p. 245°–250° C.

EXAMPLE 5 dl-5-[(2-(4-benzyloxyphenylmethyl)-3,4-dihydro-2H-benzopyran-6-yl)methyl]thiazolidine-2,4-dione The olefin prepared according to Example 4 (1.3 g) and 3% Na/Hg (20 g) were stirred in 50 ml of methanol for 18 hours. The solvent was decanted off, acidified with 25 ml of 10% HCl and extracted with ethyl acetate (2×100 ml). The combined organic phases were washed with saturated NaCl, dried over MgSO$_4$ and stripped of solvents in vacuo. The residue was purified on silica gel using hexane/ethyl acetate (3:1) as eluent to afford 1.0 g of the title compound as a solid after crystallization from hexane, m.p. 118°–120° C.

EXAMPLE 6 dl-5-[(2-(4-benzyloxyphenylmethyl)-3,4-dihydro-2H-benzopyran-6-yl)-methyl]thiazolidine-2,4-dione sodium salt 1.0 g of dl-5-[(2-(4-benzyloxyphenylmethyl)-3,4-dihydro-2H-benzopyran-6-yl)methyl]thiazolidine-2,4-dione was dissolved in 25 ml of methanol to which was added 120 mg of sodium methoxide. The mixture was stirred at room temperature for 12 hours. The methanol was concentrated in vacuo and triturated with ether to afford 900 mg of the title compound as a solid, m.p. 270°–272° C.

What is claimed is:

1. A compound of the formula

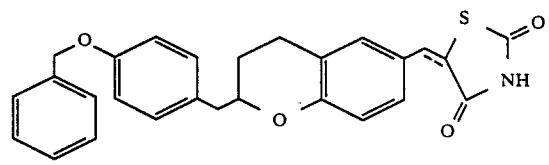

or a pharmaceutically acceptable cationic salt thereof wherein the broken line is a bond or no bond.

2. The compound according to claim 1 of the formula

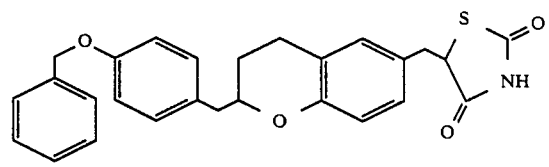

or a pharmaceutically acceptable cationic salt thereof.

3. A pharmaceutical composition for use in a hyperglycemic mammal which comprises a blood glucose lowering amount of a compound of claim 1 and a pharmaceutically acceptable carrier.

4. A pharmaceutical composition for use in a hyperglycemic mammal which comprises a blood glucose lowering amount of a compound of claim 2 and a pharmaceutically acceptable carrier.

5. A pharmaceutical composition for use in lowering serum cholesterol levels in a mammal which comprises a serum cholesterol level lowering amount of a compound of claim 2 and a pharmaceutically acceptable carrier.

6. A pharmaceutical composition for use in a hyperglycemic mammal which comprises a blood glucose lowering and serum cholesterol level lowering amount of a compound of claim 2 and a pharmaceutically acceptable carrier.

7. A method of lowering the blood glucose in a hyperglycemic mammal which comprises administering to a mammal in need of such treatment a blood glucose lowering amount of a compound of claim 1.

8. A method of lowering the blood glucose in a hyperglycemic mammal which comprises administering to a mammal in need of such treatment a blood glucose lowering amount of a compound of claim 2.

9. A method of lowering serum cholesterol levels in a mammal which comprises administering to such mammal a serum cholesterol level lowering amount of a compound of claim 2.

10. A method of lowering the blood glucose and serum cholesterol levels in a hyperglycemic mammal which comprises administering to such mammal a blood glucose lowering and serum cholesterol level lowering amount of a compound of claim 2.

* * * * *

UNITED STATES PATENT AND TRADEMARK OFFICE
CERTIFICATE OF CORRECTION

PATENT NO. : 4,791,125
DATED : December 13, 1988
INVENTOR(S) : David A. Clark

It is certified that error appears in the above-identified patent and that said Letters Patent is hereby corrected as shown below:

Columns 5-6, Synthetic Scheme A, Formula IX should read

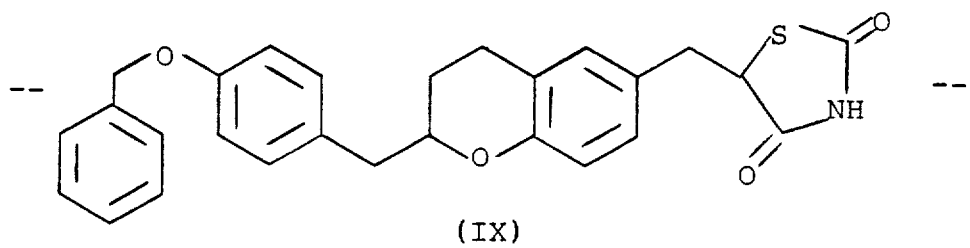

(IX)

Column 11, line 33, "78° C." should read -- -78° C. --.

Signed and Sealed this

Sixth Day of June, 1989

Attest:

DONALD J. QUIGG

Attesting Officer

Commissioner of Patents and Trademarks